United States Patent [19]

Murase et al.

[11] Patent Number: 5,236,569

[45] Date of Patent: Aug. 17, 1993

[54] AIR/FUEL RATIO SENSOR HAVING RESISTOR FOR LIMITING LEAK CURRENT FROM PUMPING CELL TO SENSING CELL

[75] Inventors: Takao Murase, Kohnan; Tsunenori Yoshimura, Nagoya, both of Japan

[73] Assignee: NGK Insulators, Ltd., Aichi, Japan

[21] Appl. No.: 617,651

[22] Filed: Nov. 26, 1990

[30] Foreign Application Priority Data

Nov. 28, 1989 [JP] Japan ................................. 1-307886

[51] Int. Cl.$^5$ ............................................. G01N 27/46
[52] U.S. Cl. ................................. 204/412; 204/410;
  204/425; 204/426; 204/431; 204/432
[58] Field of Search .............. 204/412, 425, 426, 431,
  204/432, 410

[56] References Cited

U.S. PATENT DOCUMENTS

| | | | |
|---|---|---|---|
| 4,645,572 | 2/1987 | Nishizawa et al. | 204/153.18 |
| 4,804,454 | 2/1989 | Asakura et al. | 204/406 |
| 4,818,362 | 4/1989 | Asakura et al. | 204/406 |
| 4,897,174 | 1/1990 | Wang et al. | 204/425 |
| 4,990,235 | 2/1991 | Chujo | 204/424 |
| 5,028,309 | 7/1991 | Nishizawa et al. | 204/425 |
| 5,032,248 | 7/1991 | Kanamaru et al. | 204/429 |
| 5,080,765 | 1/1992 | Wang et al. | 204/153.1 |

FOREIGN PATENT DOCUMENTS 2093320 8/1982 United Kingdom .

*Primary Examiner*—John Niebling
*Assistant Examiner*—Arun S. Phasge
*Attorney, Agent, or Firm*—Parkhurst, Wendel & Rossi

[57] ABSTRACT

An air/fuel ratio sensor with a sensing element having an electrochemical oxygen pumping cell including a first oxygen ion-conductive solid electrolyte body, and a first and a second electrode formed on the first solid electrolyte body, an electrochemical oxygen sensing cell including a second oxygen ion-conductive solid electrolyte body, and a third and a fourth electrode formed on the second solid electrolyte body, the second and third electrodes being exposed to exhaust gases which are produced as a result of combustion of an air-fuel mixture and which are introduced into the sensing element, under a predetermined diffusion resistance. One of the first and second electrodes is connected to a reference conductor having a reference potential for permitting a pump current to flow through the oxygen pumping cell, while the third electrode is connected to the reference conductor via an electrical resistor so that an amount of a leak current which leaks from the oxygen pumping cell to the oxygen sensing cell is determined by an electrical resistance value of the electrical resistor.

14 Claims, 6 Drawing Sheets

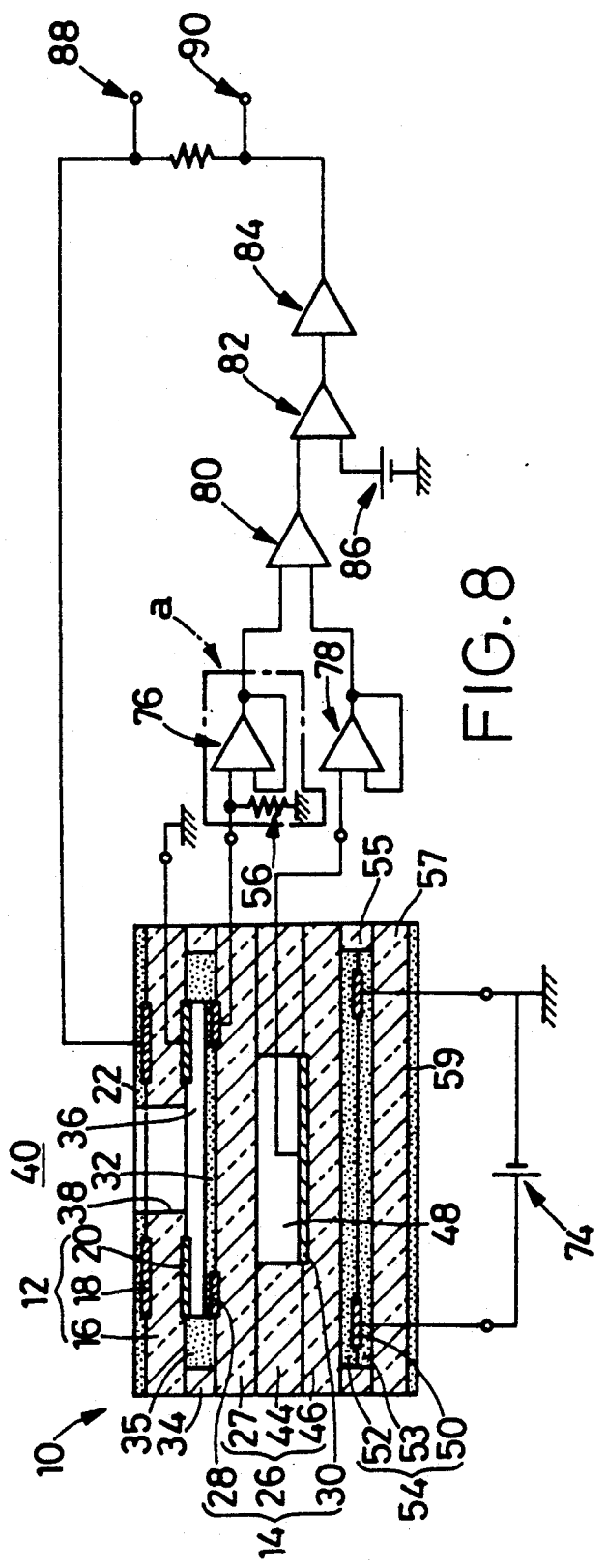
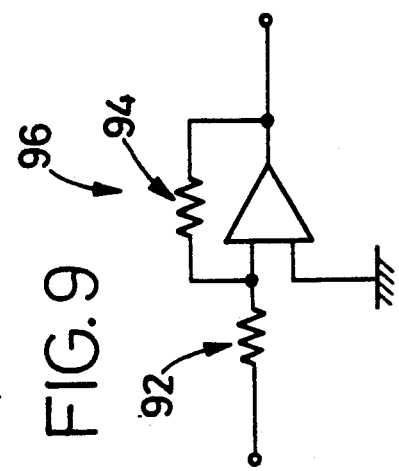
FIG. 8
FIG. 9

AIR/FUEL RATIO SENSOR HAVING RESISTOR FOR LIMITING LEAK CURRENT FROM PUMPING CELL TO SENSING CELL

BACKGROUND OF THE INVENTION

1. Field of the Invention

The present invention relates in general to an oxygen sensing apparatus adapted to detect an oxygen concentration of combustion exhaust gases such as those emitted by internal combustion engines of automobiles or various industrial furnaces, and more specifically to such an oxygen sensor used for a combustion control system for internal combustion engines and industrial furnaces, to determine an air/fuel (A/F) ratio of an air-fuel mixture supplied to the engines and furnaces.

2. Discussion of the Prior Art

Various types of oxygen sensors are known for determining an oxygen concentration of combustion exhaust gases emitted for example by automotive internal combustion engines, industrial furnaces or boilers. For instance, there is known a sensor which utilizes a zirconia ceramic or other oxygen-ion conductive solid electrolyte material and which is operated to determine the oxygen concentration according to the principle of an oxygen concentration cell. For operating an internal combustion engine, it is required to accurately control an air/fuel (A/F) ratio of an air-fuel mixture supplied to the engine, such that the actual air/fuel ratio coincides with a desired or nominal value. Generally, this air/fuel ratio is determined by measuring the concentration of oxygen in the exhaust gases, which is varied as a function of the air/fuel ratio of the air-fuel mixture supplied to the engine. A signal representative of the air/fuel ratio is fed to a fuel supply control system of the engine, in order to determine an amount of supply of the fuel, i.e., to control the fuel supply in a feedback manner so that the actual air/fuel ratio coincides with the desired value.

As one type of such an oxygen sensor used as an A/F-ratio sensor, there is known a so-called double-cell type sensor having two electrochemical cells, that is a pumping cell and a sensing cell, as disclosed in laid-open Publication No. 59-190652 of unexamined Japanese Patent Application. The A/F-ratio sensor of this type is capable of dealing with not only stoichiometric exhaust gases emitted by combustion of an air-fuel mixture whose A/F ratio is equal to or near the stoichiometric value (A/F=14.6), but also lean-burned or rich-burned exhaust gases emitted by combustion of a fuel-lean or fuel-rich air-fuel mixture whose A/F ratio is larger or smaller than the stoichiometric value. In this double-cell type A/F-ratio sensor, a sensing element of the sensor is formed with an internal gas-diffusion space into which a measurement gas (exhaust gases) is introduced from an external measurement-gas space under a predetermined diffusion resistance. The electrochemical oxygen sensing cell includes a measuring electrode exposed to the atmosphere within the internal gas-diffusion space, and a reference electrode exposed to a reference atmosphere which has a predetermined oxygen partial pressure. This sensing cell produces an output in the form of an electromotive force which is induced according to the principle of an oxygen concentration cell. The electrochemical oxygen pumping cell includes an outer pumping electrode exposed to the measurement gas existing in the external measurement-gas space, and an inner pumping electrode exposed to the atmosphere within the internal gas-diffusion space. This oxygen pumping cell is operated to effect a pumping action so as to control the atmosphere in the internal gas-diffusion space. The sensing element constructed as described above is adapted to measure the oxygen concentration of the measurement gas based on a pump current applied to the oxygen pumping cell to effect the pumping action so as to control the oxygen concentration of the atmosphere within the internal gas-diffusion space such that the electromotive force produced by the oxygen sensing cell coincides with a predetermined value.

If there arises a difference in the oxygen partial pressure between the atmosphere (within the gas-diffusion space) which contacts the measuring electrode of the oxygen sensing cell, and the atmosphere (within the gas-diffusion space) which contacts the inner pumping electrode of the oxygen pumping cell, the A/F-ratio sensor of the above type suffers from reduction in the operating response and deterioration of the oxygen pumping cell.

In view of the above, there is proposed a method of determining the concentration of a given component (such as oxygen) in the measurement gas, as disclosed in U.S. Pat. No. 4,645,572 (laid-open Publication No. 61-194345 of unexamined Japanese Patent Application). In the oxygen sensor disclosed therein, a first solid electrolyte body for the oxygen sensing cell and a second solid electrolyte body for the oxygen pumping cell are electrically connected to each other through a solid electrolyte layer interposed therebetween. Further, the measuring electrode of the sensing cell and one of the inner and outer electrodes of the pumping cell are connected to a reference conductor (e.g., the earth) which provides a reference potential for permitting a pump current to flow through the pumping cell. With the measuring and inner or outer pumping electrodes having the same potential, a portion of the pump current applied to the oxygen pumping cell leaks toward the measuring electrode of the oxygen sensing cell. In this arrangement, an auxiliary pumping action is effected at the measuring electrode of the oxygen sensing cell, by the leak current which leaks from the oxygen pumping cell. Consequently, the oxygen sensor of this type is capable of compensating the sensor output for the difference between the oxygen partial pressure of the atmosphere which contacts or surrounds the measuring electrode, and the atmosphere which contacts or surrounds the inner pumping electrode.

However, a further analysis by the present inventors of the oxygen sensor of the above type revealed that the leak current which flows from the oxygen pumping cell toward the oxygen sensing cell causes a potential change in the oxygen sensing cell due to a resistance potential drop, whereby the sensing accuracy of the oxygen sensor is lowered. In addition, since the amount of the potential change due to the resistance potential drop is varied with the internal resistance value of the solid electrolyte body of the sensing cell, the sensing accuracy of the sensor tends to be largely dependent on the temperature of the sensing cell.

Further, the auxiliary pumping action of the measuring electrode by the leak pump current causes a potential drop of the measuring electrode upon ionization of oxygen ($O_2$). This potential drop changes the output characteristic of the oxygen sensing cell and lowers the sensing accuracy of the oxygen sensor. The amount of this potential drop of the measuring electrode due to the auxiliary pumping action is likely to be influenced by the surface condition of the measuring electrode or surface condition of a protecting layer covering the electrode, that is, influenced by a change in the gas diffusion resistance around the measuring electrode. More specifically, if the gas diffusion resistance is changed by gas absorption or deposition of foreign particles during use of the sensor, the output characteristic of the oxygen sensor is remarkably changed, making it difficult to assure sufficiently high chronological operating stability and reliability of the sensor.

The lowered operating accuracy of the sensor or the chronological change of the output characteristic of the sensor, which results from leaking of the pump current from the oxygen pumping cell toward the oxygen sensing cell, is particularly serious when the pump current is relatively high, that is, when the oxygen sensor as the A/F-ratio sensor is used to deal with lean-burned or rich-burned exhaust gases emitted by combustion of an air-fuel mixture whose A/F ratio is larger or smaller than the stoichiometric value. Thus, there remains room for improvement in the known oxygen sensor as described above.

SUMMARY OF THE INVENTION

The present invention was developed in view of the problems encountered in the known A/F-ratio sensor as described above. It is therefore an object of the present invention to provide an improved air/fuel ratio sensing apparatus capable of dealing with lean-burned and/or rich-burned exhaust gases, which apparatus is adapted to effect an auxiliary oxygen pumping action by a leak pump current leaking from the oxygen pumping cell toward the oxygen sensing cell, for eliminating a difference in the oxygen partial pressure between the atmospheres surrounding the measuring electrode of the sensing cell and the inner pumping electrode of the pumping cell, such that the leak pump current has a reduced or minimum adverse influence on the sensing accuracy and chronological operating stability or output characteristic of the apparatus.

The above object may be achieved according to the principle of the present invention, which provides an air/fuel ratio sensing apparatus for determining an air/fuel ratio of an air-fuel mixture, including: a sensing element including an electrochemical oxygen pumping cell having a first oxygen ion-conductive solid electrolyte body and a first and a second electrode which are formed on the first solid electrolyte body, an electrochemical oxygen sensing cell having a second oxygen ion-conductive solid electrolyte body and a third and a fourth electrode which are formed on the second solid electrolyte body; and diffusion-resistance means for introducing exhaust gases produced as a result of combustion of the air-fuel mixture, under a predetermined diffusion resistance, for contact with the second electrode of the pumping cell and the third electrode of the sensing cell. The apparatus comprises: means for connecting one of the first and second electrodes of the oxygen pumping cell to a reference conductor having a reference potential for permitting a pump current to flow through the oxygen pumping cell; and an electrical resistor provided in a conductor path connecting the third electrode of the sensing cell to the reference conductor, so that an amount of a leak current which leaks from the oxygen pumping cell to the oxygen sensing cell is determined by an electrical resistance value of the electrical resistor.

Experiments and study by the applicants of the double-cell type air/fuel ratio sensor revealed the following two points:

A difference in the partial pressure of a gas component between the atmosphere adjacent to the measuring electrode (third electrode) of the oxygen sensing cell and the atmosphere adjacent to the inner electrode (second electrode) of the oxygen pumping cell is relatively small, and therefore an auxiliary pumping action by the measuring and inner pumping electrodes by a leak pump current is sufficiently effective to compensate the sensor output for the above partial pressure difference, even if the amount of the leak pump current is relatively small. By reducing the amount of the leak pump current, the resistance potential drop of the sensing cell due to the leak pump current and the potential drop of the measuring electrode due to ionization of oxygen ($O_2$) by the leak pump current may be effectively reduced, and the sensing accuracy and the chronological output characteristic stability may be accordingly improved. The present invention was developed based on the above findings.

In the air/fuel ratio sensing apparatus of the present invention constructed as described above, the electrical resistor is provided in the conductor path between the third electrode of the oxygen sensing cell, and the reference conductor which has a reference potential for permitting the pump current to flow between the first and second electrodes of the oxygen pumping cell. Consequently, the potential difference between the first or second electrode and the third electrode to which a portion of the pump current leaks from the first or second electrode is smaller by the amount corresponding to the potential drop by the resistor, than the potential difference between the first and second electrodes between which the pump current flows.

Therefore, the amount of the leak pump current can be made relatively small, depending upon the resistance value of the resistor. Accordingly, the deterioration of the sensing accuracy and chronological output stability of the apparatus can be avoided or minimized, while assuring an effective auxiliary pumping action for improving the operating response of the apparatus, by utilizing the auxiliary pump current which leaks from the pumping cell to the third electrode of the sensing cell.

The electrical resistor may be provided as an integral part of the sensing element of the apparatus, or incorporated in an electrical circuit of the apparatus, which is disposed outside the sensing element and electrically connected thereto.

For improving the sensing accuracy and output stability of the apparatus, it is desirable that the electrical resistance value of the electrical resistor be determined such that a ratio of the amount of the leak current to an overall amount of the pump current applied to the oxygen pumping cell is within a range of 0.1–5%, preferably within a range of 0.5–3%.

The second electrode of the oxygen pumping cell which is exposed to the introduced exhaust gases may be connected to the reference conductor. The third electrode of the oxygen sensing cell may be connected via the electrical resistor to the earth which serves as the reference conductor. The one of the first and second electrodes of the oxygen pumping cell which is connected to the reference conductor may be connected to the third electrode of the oxygen sensing cell via the electrical resistor.

Where a heater having a heat-generating element for heating the oxygen pumping and sensing cells is provided, the electrical resistor may be connected to the reference conductor via a terminal through which the heat-generating element of the heater is connected to a heater power source for energization of the heat-generating element. Alternatively, the electrical resistor may be connected to a conductor path between the third electrode of the oxygen sensing cell and a differential amplifier which receives outputs of the third and fourth electrodes of the oxygen sensing cell and which produces an output indicative of an electromotive force induced between the third and fourth electrodes.

A connecting or intermediate solid electrolyte body may be interposed between the first and second solid electrolyte bodies of the oxygen pumping and sensing cells, so that the connecting solid electrolyte body and the first and second solid electrolyte bodies cooperate to define a gas-diffusion space as the diffusion resistance means. The gas-diffusion space may be a thin flat space. In this case, the second and third electrodes of the oxygen pumping and sensing cells may be disposed opposite to each other in a direction of thickness of the thin flat space, so as to partially define the thin flat space.

BRIEF DESCRIPTION OF THE DRAWINGS

The above and other objects, features and advantages of the present invention will be better understood by reading the following detailed description of presently preferred embodiments of the invention, when considered in connection with the accompanying drawings, in which:

FIG. 8 is a schematic elevational view in cross section of a sensing element of an oxygen sensor constructed according to another embodiment of the invention; and FIG. 9 is a view showing an inverting amplifier including two resistors, which may be used in the oxygen sensor of FIG. 8 instead of the electrical arrangement as indicated by an arrow "a".

DETAILED DESCRIPTION OF THE PREFERRED EMBODIMENTS

Figure 1:
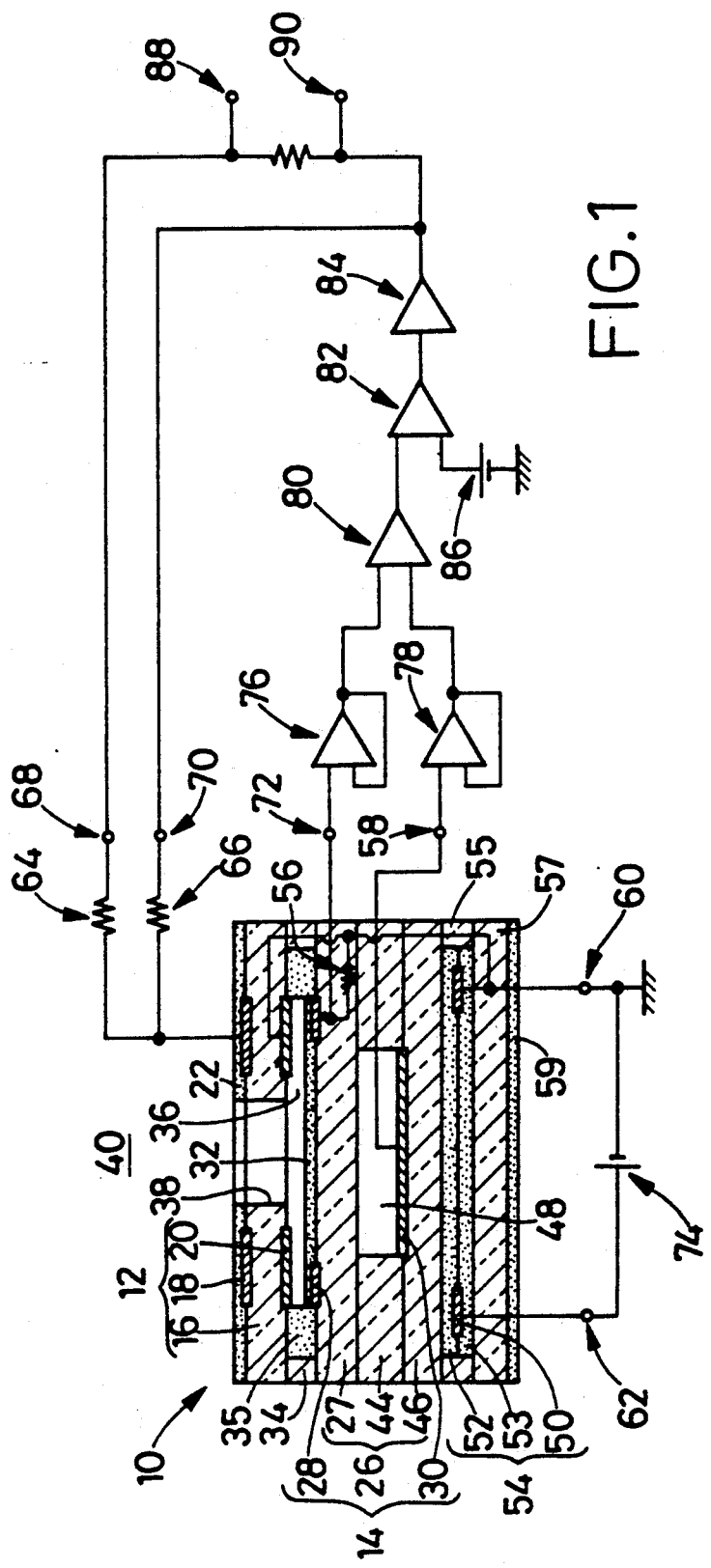
FIG. 1 is a schematic elevational view in cross section of a sensing element of one embodiment of an oxygen sensor of the present invention in the form of an A/F-ratio sensing apparatus.
Figure 2:
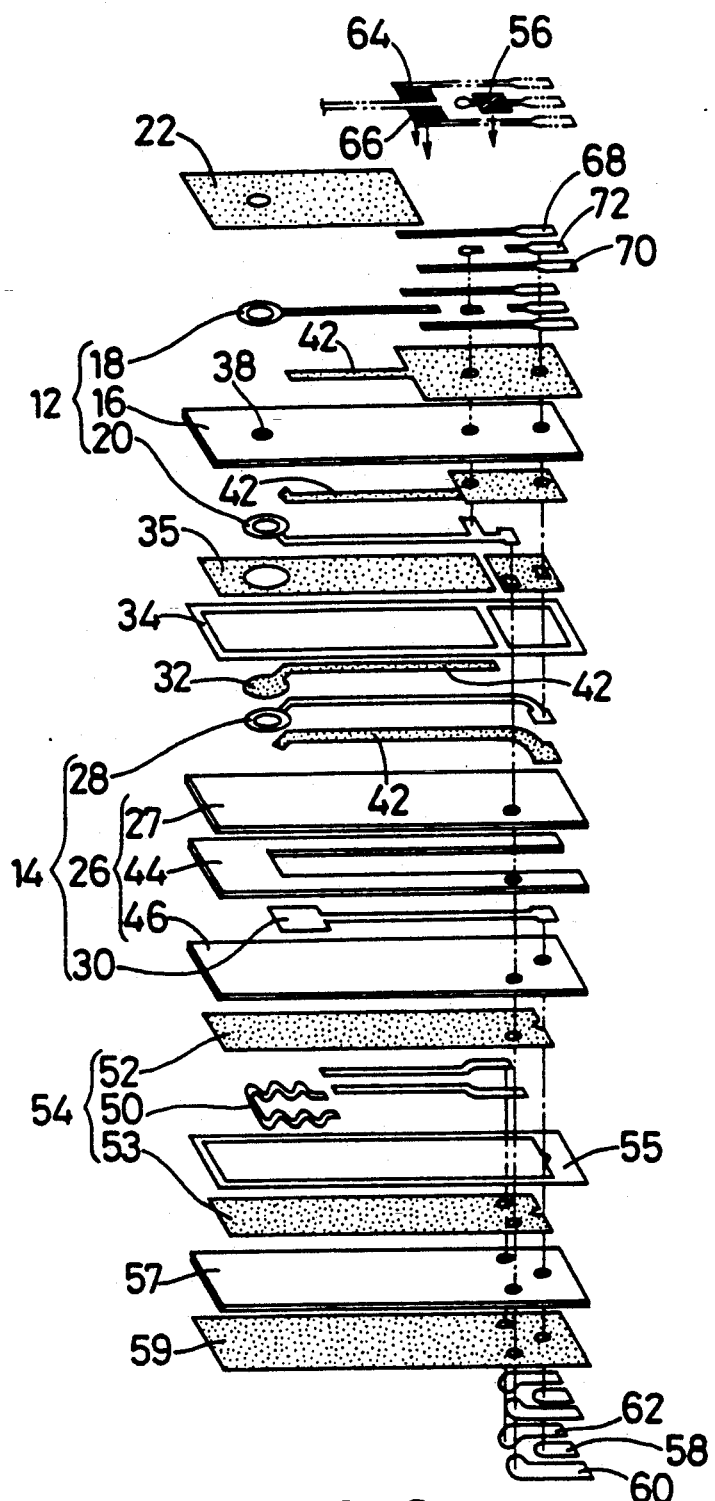
FIG. 2 is a perspective view illustrating the structure of the sensing element of the oxygen sensor of FIG. 1.

Referring first to the schematic views of FIGS. 1 and 2, reference numeral 10 denotes a sensing element of the oxygen sensor in the form of an A/F-ratio sensing apparatus constructed according to one embodiment of the present invention. The sensing element 10 has an electrochemical oxygen pumping cell 12 and an electrochemical oxygen sensing cell 14 which will be described in detail below.

The oxygen pumping cell 12 consists of a generally elongate planar first solid electrolyte body 16, and an outer pumping electrode (first electrode) 18 and an inner pumping electrode (second electrode) 20 which are formed on the opposite major surfaces of the first solid electrolyte body 16 such that the electrodes 18, 20 are aligned with each other as viewed in a direction perpendicular to the plane of the solid electrolyte body 16. The first solid electrolyte body 16 is formed of an oxygen-ion conductive solid electrolyte such as zirconia ceramics containing yttria. The outer and inner pumping electrodes 18, 20 are formed of a metal such as platinum, or a cermet thereof, which metal or cermet serves as a catalyst for promoting an electrochemical reaction of oxygen. The outer surfaces of the first solid electrolyte body 16 and the outer pumping electrode 18 are covered by a porous protecting layer 22 which is formed of a suitable electrically insulating material such as alumina, such that the solid electrolyte body 16, the electrodes 18, 20 and the protecting layer 22 constitute an integral laminar structure.

Like the oxygen pumping cell 12 as described above, the oxygen sensing cell 14 consists of a generally elongate planar second solid electrolyte body 26, and a measuring electrode (third electrode) 28 and a reference electrode (fourth electrode) 30 which are formed in contact with the second solid electrolyte body 26. The second electrolyte body 26 is formed of zirconia ceramics containing yttria, for example, and consists of three solid electrolyte layers 27, 44, 46 which are laminated on each other in the direction of thickness thereof. The measuring and reference electrodes 28, 30 are also formed of a metal such as platinum or a cermet. A porous protecting layer 32 made of alumina, for example, is formed integrally to cover the outer surfaces of the measuring electrode 28 and a portion of the upper layer 27 of the second solid electrolyte body 26.

Between the oxygen pumping cell 12 and the oxygen sensing cell 14, there are interposed a generally frame-like connecting solid electrolyte layer 34 formed of an oxygen-ion conductive solid electrolyte such as zirconia ceramics containing yttria, and an electrically insulating layer 35 formed of a suitable electrically insulating material such as alumina, such that the insulating layer 35 is disposed in the same plane with and inside the frame of the connecting solid electrolyte layer 34, as shown in FIG. 2. With these layers 34, 35 interposed between the first and second solid electrolyte bodies 16, 26 of the oxygen pumping and sensing cells 12, 14, there is defined a gas-diffusion space in the form of a thin, circular flat space 36 which serves as diffusion resistance means having a predetermined resistance to diffusion of a gas. That is, the thin flat space 36 has the same thickness as the connecting solid electrolyte layer 34 (electrically insulating layer 35). The central portion of the thin flat space 36 communicates through a gas-inlet aperture 38 with an external measurement-gas space 40 in which exhaust gases exist as a measurement gas to be dealt with by the present A/F-ratio sensing apparatus. The gas-inlet aperture 38 is formed through the thicknesses of the first solid electrolyte body 6 and the porous protecting layer 22. In operation, the exhaust gases in the external measurement-gas space 40 are introduced through the gas-inlet aperture 38, and diffuses into the thin flat space 36 under the predetermined resistance.

The second solid electrolyte body 26 of the oxygen sensing cell 14 has an elongate rectangular air passage 48 formed therein parallel to its plane, so as to extend in the longitudinal direction and communicate with the ambient air as a reference gas. More specifically, the intermediate layer 44 of the second solid electrolyte body 26 has an elongate rectangular slot which cooperates with the upper and lower layers 27, 46 to define the air passage 48. The above-indicated reference electrode 30 is formed on the lower layer 46 of the second solid electrolyte body 26, such that the electrode 30 is exposed to the passage 48 communicating with the ambient air.

The outer electrode 18 of the oxygen pumping cell 12 is exposed to the external measurement-gas space 40, that is, to the measurement gases or exhaust gases present in the space 40, through the porous protecting layer 22. The inner electrode 20 of the oxygen pumping cell 12 and the measuring electrode 28 of the oxygen sensing cell 14 are exposed to the circular flat space 36, such that these electrodes 20, 28 are held in communication or contact with the atmosphere within the flat space 38, which consists of the measurement gas that is introduced under the predetermined diffusion resistance. Further, the reference electrode 30 of the oxygen sensing cell 14 is exposed to the air passage 48, and is held in communication or contact with the ambient air present in the air passage 48. The electrodes 18, 20, 28 of the oxygen pumping and sensing cells 12, 14 are connected via respective electrical leads to an external electric circuit which will be described later. As shown in FIG. 2, an electrically insulating layer 42 is interposed between the electrical lead for each of the electrodes 18, 20, 28 and the first or second solid electrolyte body 16, 26 on which the electrode 18, 20, 28 is formed.

On the outer major surface of the lower layer 46 of the second solid electrolyte body 26 remote from the oxygen pumping cell 12, there is formed a ceramic heater 54 having a laminar structure which includes a heat-generating element 50 and two electrically insulating ceramic layers 52, 53 sandwiching the heat-generating element 50. This ceramic heater 54 is adapted to heat the oxygen pumping and sensing cells 12, 14 to a suitable operating temperature. The ceramic heater 54 is surrounded at its outer periphery by a gas-tight ceramic frame 55, and is sandwiched by and between the lower solid electrolyte layer 46 and a gas-tight ceramic plate 57 whose outer surface is covered by an electrically insulating layer 59.

In the sensing element 10 of the oxygen sensor as described above, the electrical lead of the outer electrode 18 of the oxygen pumping cell 12 is connected through a first and a second shunt resistor 64, 66 to respective external connecting terminals 68, 70, while the electrical lead of the measuring electrode 28 of the oxygen sensing cell 14 is connected to an external connecting terminal 72. Further, the electrical leads of the measuring electrode 28 and the inner pumping electrode 20 are connected to each other through an electrical resistor 56, such that a portion of the electrical lead which is located between the resistor 56 and the measuring electrode 28 is connected to the above-indicated external connecting terminal 72, and such that a portion of the electrical lead which is located between the resistor 56 and the inner pumping electrode 20 is connected to another external connecting terminal 60. Further, this connecting terminal 60 and an external connecting terminal 62 are connected to the above-indicated heat-generating element 50, so that a heater current is applied through these connecting terminals 60, 62 to the heat-generating element 50, so as to energize the heat-generating element 50.

Each of the first and second shunt resistors 64, 66 and the resistor 56 is formed by printing using a known thick-film paste for a thick-film resistor, on a sintered body of the sensing element 10, and firing the applied paste so that the obtained resistors 64, 66, 56 cover a portion of the appropriate electrical lead formed on the insulating layer 42, as shown in FIG. 2.

The thus constructed sensing element 10 of the oxygen sensor is electrically connected to the external electric circuit as shown in FIG. 1, which governs various electrical operations of the sensing element 10. More specifically, the external connecting terminal 60 is grounded, i.e., is connected to a reference conductor for providing a reference potential, such as a body of a motor vehicle or the earth. With the connecting terminal 60 being grounded, the potential of the inner electrode 20 of the oxygen pumping cell 12 is set to a reference point (reference potential) for a pump current which is applied between the outer and inner electrodes 18, 20 through the first solid electrolyte body 16. On the other hand, the measuring electrode 28 of the oxygen sensing cell 14 is grounded via the resistor 56, so that the measuring electrode 28 has a potential which is different from the reference potential, due to the presence of the resistor 56 which causes a potential drop between the measuring electrode 28 and the reference conductor (e.g., the earth). The difference between the reference potential and the potential of the measuring electrode 28 corresponds to the amount of the potential drop caused by the resistor 56. In other words, the resistor 56 is adapted to give a suitable amount of electrical resistance to a conductor path between the measuring electrode 28 and the reference conductor, so that the electrical resistance value of the above conductor path is made larger than the resistance value of a conductor path between the inner pumping electrode 20 and the reference conductor. Thus, the measuring electrode 28 is provided with a potential which is higher than that of the inner pumping electrode 20. Accordingly, the potential difference between the outer or inner pumping electrode 18, 20 and the measuring electrode 28 is smaller than the potential difference between the outer and inner pumping electrodes 18, 20.

The external connecting terminals 60, 62 described above are connected to an external DC power source 74, so that the heater current is applied from the DC power source 74 to the heat-generating element 50 through the connecting terminals 60, 62 so as to energize the element 50.

The external connecting terminal 72, 58 which are connected to the measuring and reference electrodes 28, 30 of the oxygen sensing cell 14, respectively, are connected through respective amplifiers 76, 78 to a differential amplifier 80. Namely, the amplifiers 76, 78 produce outputs representative of the potentials of the measuring and reference electrodes 28, 30, respectively, which potentials are varied depending upon the oxygen concentration of the atmosphere within the thin flat space 36. The outputs of the amplifiers 76, 78 are fed to the differential amplifier 80, which produces an output representative of a potential difference between the measuring and reference electrodes 28, 30.

To the output of the differential amplifier 80, there is connected a comparator 82, whose output is connected to a V-I converter 84. The output of the V-I converter 84 is connected through two separate conductor paths to the above-indicated external connecting terminals 68, 70 that are connected to the outer electrode 18 of the oxygen pumping cell 12. In this arrangement, the output of the differential amplifier 80 which represents the potential difference between the electrodes 28, 30 of the oxygen sensing cell 14 is fed to the comparator 82, which compares the received potential difference with a reference voltage 86 and produces a voltage indicative of the result of the comparison. Then, the voltage produced by the comparator 82 is converted by the V-I converter 84 into a corresponding positive or negative current, which is utilized as the pump current to be applied to the oxygen pumping cell 12.

Thus, as well known in the art, the external electric circuit is adapted such that the pump current which is determined based on an electromotive force produced by the oxygen sensing cell 14 is applied to the oxygen pumping cell 12, so that the oxygen pumping cell 12 performs an oxygen pumping action so as to maintain the oxygen concentration of the atmosphere in the flat space 36 at a predetermined value. This predetermined value corresponds to the stoichiometric point (14.6) of an A/F ratio of an air-fuel mixture which produces the exhaust gases as the measurement gas as a result of its combustion. Accordingly, the oxygen concentration of the measurement gas in the external measurement-gas space 40 can be determined based on the pump current as detected between two output terminals 88, 90 provided between the V-I converter 84 and one of the connecting terminals 68, 70 which are connected to the outer pumping electrode 18. In the present embodiment, the output terminals 88, 90 are provided in the conductor path between the converter 84 and the connecting terminal 68.

It is to be noted that the amount of the pump current is determined by detecting a current which flows through one of the two conductor paths for connecting the V-I converter 84 and the outer pumping electrode 18. Namely, the amounts of the currents which flow through these two conductor paths can be changed relative to each other by suitably determining the resistance values of the first and second shunt resistors 64, 66. Accordingly, suitable determination of the resistance values of the two shunt resistors 64, 66 permits the sensing elements of the individual oxygen sensors to have substantially the same relationship between the amount of the pump current and the oxygen concentration of the measurement gas. In other words, an otherwise possible error in the actual relationship of each oxygen sensing element from the nominal relationship may be eliminated by suitably determining the resistance values of the shunt resistors 64, 66.

The first solid electrolyte body 16 of the oxygen pumping cell 12 and the second solid electrolyte body 26 of the oxygen sensing cell 14 are electrically connected in part with each other via the connecting solid electrolyte layer 34. During the sensing operation of the present oxygen sensor, therefore, a portion of the pump current leaks from the oxygen pumping cell 12 to the oxygen sensing cell 14, in other words, a leak current flows from the outer pumping electrode 18 toward the measuring electrode 28 or vice versa. Consequently, the outer pumping electrode 18 and the measuring electrode 28 cooperate with the first and second solid electrolyte bodies 16, 26 to perform an auxiliary pumping action with the leak current flowing between the electrodes 18, 28.

In the sensing element 10 as described above, the measuring electrode 28 is connected via the resistor 56 to the reference conductor for providing the reference potential, while the inner electrode 20 of the oxygen pumping cell 12 is directly connected to the same reference conductor. Accordingly, the potential of the measuring electrode 28 is different from that of the inner pumping electrode 20 by a predetermined value which corresponds to the amount of the potential drop caused by the resistor 56. By suitably determining the resistance value of the resistor 56, therefore, it is possible to restrain or limit the amount of the above-indicated leak current or auxiliary pumping current which flows between the outer pumping electrode 18 and the measuring electrode 28.

Figure 3:
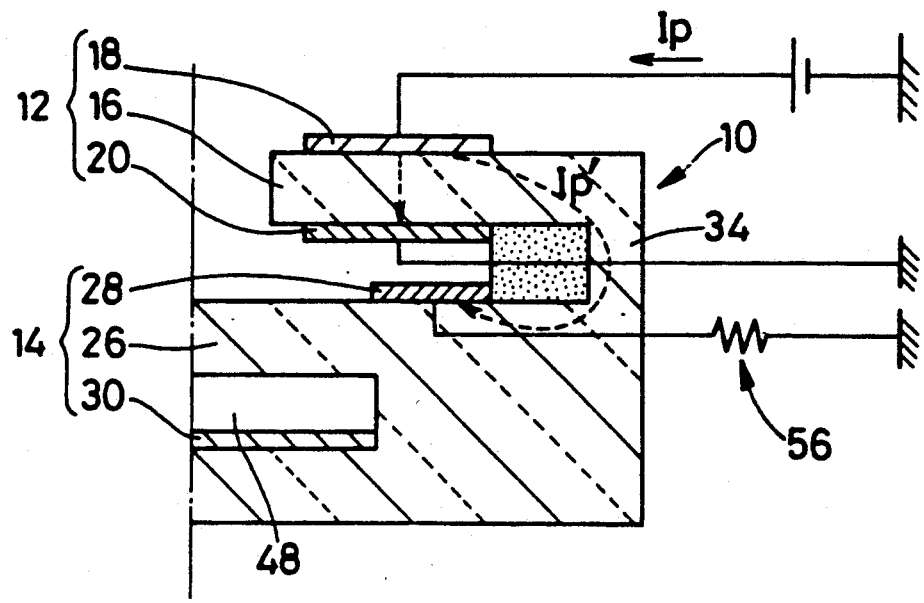
FIG. 3 is a fragmentary elevational view illustrating an example of electric operations of the oxygen sensor of FIG. 1.

More specifically described, when the measurement gas is a lean-burned exhaust gas produced as a result of combustion of a fuel-lean air-fuel mixture whose A/F ratio is larger than the stoichiometric value (A/F=14.6), the potential of the outer pumping electrode 18 has a positive value which is higher than the reference potential (zero potential), i.e., higher than the potential of the inner pumping electrode 20. Accordingly, the leak current as a portion of the pump current flows from the outer pumping electrode 18 toward the measuring electrode 28 of the oxygen sensing cell 14, as shown in FIG. 3. In this case, the resistor 56 is provided to set the potential of the measuring electrode 28 at a positive value which is higher by a given amount than the reference potential, whereby the amount of the leak current indicated above can be effectively limited or reduced or suitably determined. In this respect, the ratio of the leak current to the overall pump current can be controlled by suitably determining the resistance value of the resistor 56.

When the measurement gas is a rich-burned exhaust gas produced as a result of combustion of a fuel-rich air-fuel mixture whose A/F ratio is smaller than the stoichiometric value, on the other hand, the potential of the outer pumping electrode 18 has a negative value which is lower than the reference potential applied to the inner pumping electrode 20. Accordingly, the leak current and auxiliary pumping current flow from the inner pumping electrode 20 and the measuring electrode 28 toward the outer pumping electrode 18 of the oxygen pumping cell 12. In this case, the resistor 56 also serves to set the potential of the measuring electrode 28 at a given value which is lower by a given amount than the reference potential, whereby the amount of the leak current indicated above can be effectively restrained or reduced or suitably determined, and the ratio of the leak current to the pump current can be suitably determined.

As described above, the resistor 56 is provided to effectively limit or control the amount of the leak current which flows from the outer pumping electrode 18 toward the measuring electrode 28. Consequently, the provision of the resistor 56 reduces the resistance potential drop of the oxygen sensing cell 14 conventionally experienced due to the leak current, whereby the present oxygen sensor is less likely to or does not suffer from the problems caused by the resistance potential drop, such as deterioration in the sensing accuracy or increase in the temperature dependence of the sensing element. The provision of the resistor 56 also permits reduction in the potential drop of the measuring electrode 28 caused by the auxiliary pumping action by the leak current from the oxygen pumping cell 12. Therefore, the present oxygen sensor is less likely to or does not suffer from the problems caused by the potential drop of the measuring electrode 28, such as deterioration in the sensing accuracy or a chronological change in the operating characteristics.

It is desirable to determine the resistance value of the resistor 56 so that the ratio of the amount of the leak current (Ip') to the whole amount of the pump current applied to the oxygen pumping cell 12 is held within a range of 0.1% ~5%, preferably, within a range of 0.5% ~3%. The thus controlled leak current has a significantly reduced influence on the output characteristics of the oxygen sensing cell 14.

If the ratio (Ip'/Ip) of the leak current to the overall pump current is lower than 0.1%, that is, if the amount of the leak current is excessively small, the oxygen sensor does not enjoy sufficient effects due to the auxiliary pumping action by the leak current, for example, improvement in the operating response of the sensor. Further, in the above case where the ratio (Ip'/Ip) is smaller than 0.1%, a variation of the electromotive force of the oxygen sensing cell 14 responsive to a variation in the pump current is delayed by a phase difference of not less than $\pi$, since a system of controlling the oxygen sensor is constituted by a closed circuit which consists of a sensing portion and an amplifying portion. Consequently, oscillations may occur in the system of feedback between the sensing and amplifying portions of the control system. While the oscillations which occur in the feed-back system can be avoided by lowering the gain of the amplifying portion, the thus lowered gain may lead to deterioration in the sensing accuracy and operating response of the feed-back system. If the above ratio (Ip'/Ip) is higher than 0.1%, however, the delay of the phase of variation in the electromotive force of the oxygen sensing cell 14 with respect to that of variation in the pumping current is equal to or smaller than $\pi$. Therefore, the oxygen sensor does not suffer from the above problem, and the occurrence of the oscillations can be avoided. If the ratio (Ip'/Ip) exceeds 5%, the influence of the leak current on the electromotive force of the oxygen sensing cell 14 is rapidly increased. For the reasons as described above, when the ratio (Ip'/Ip) is held within the range of 0.1% ~5%, the influence of the leak current on the output characteristics of the sensing cell 14 can be most effectively minimized.

Figure 4:
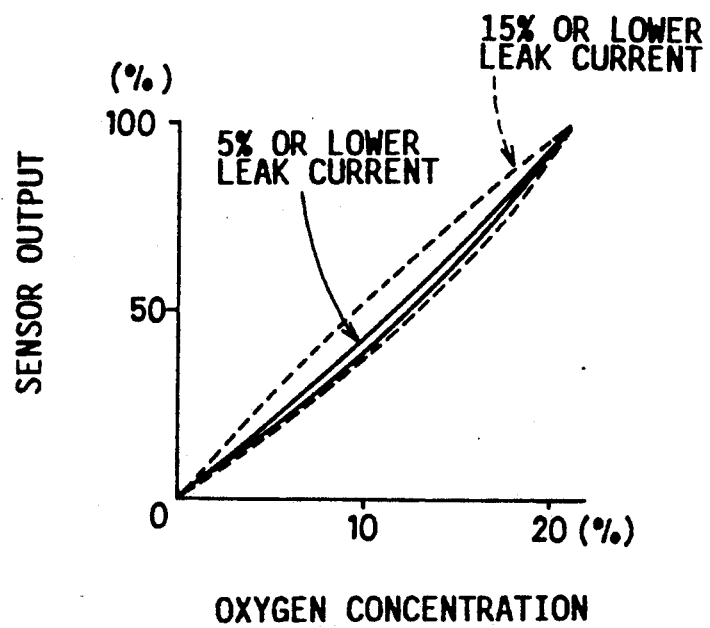
FIGS. 4 through 7 are graphs illustrating output characteristics and sensing accuracy of some specimens of the oxygen sensor similar to that of FIG. 1, which specimens have different ratios of the leak current to the pump current.
Figure 5:
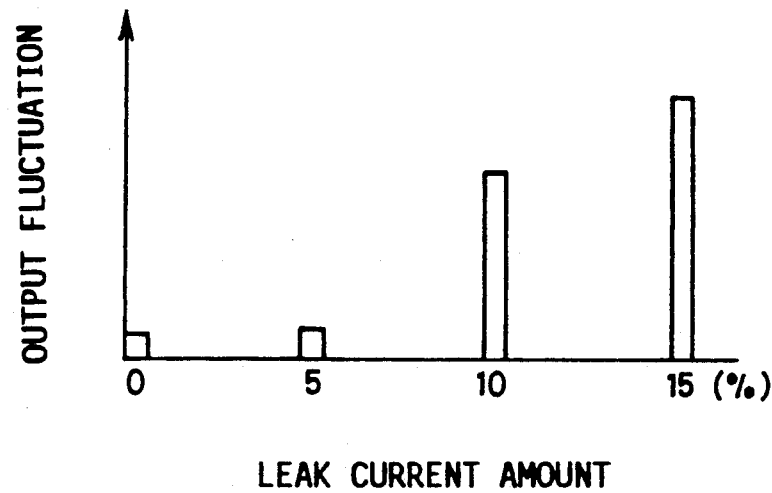
Figure 6:
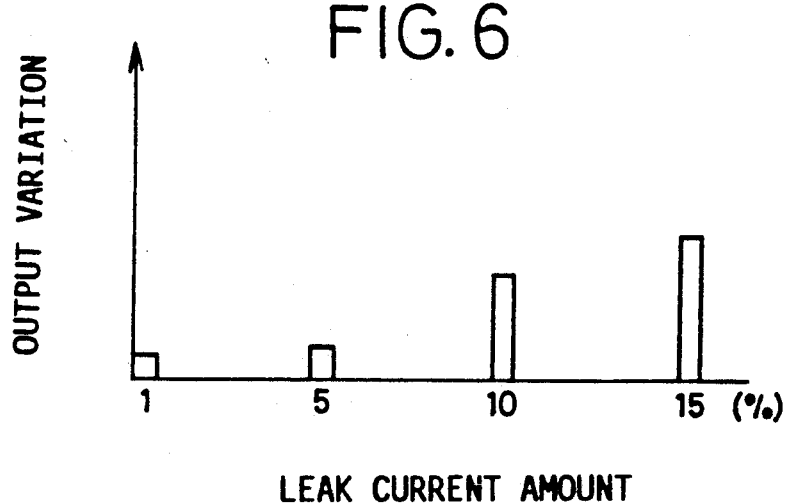
Figure 7:
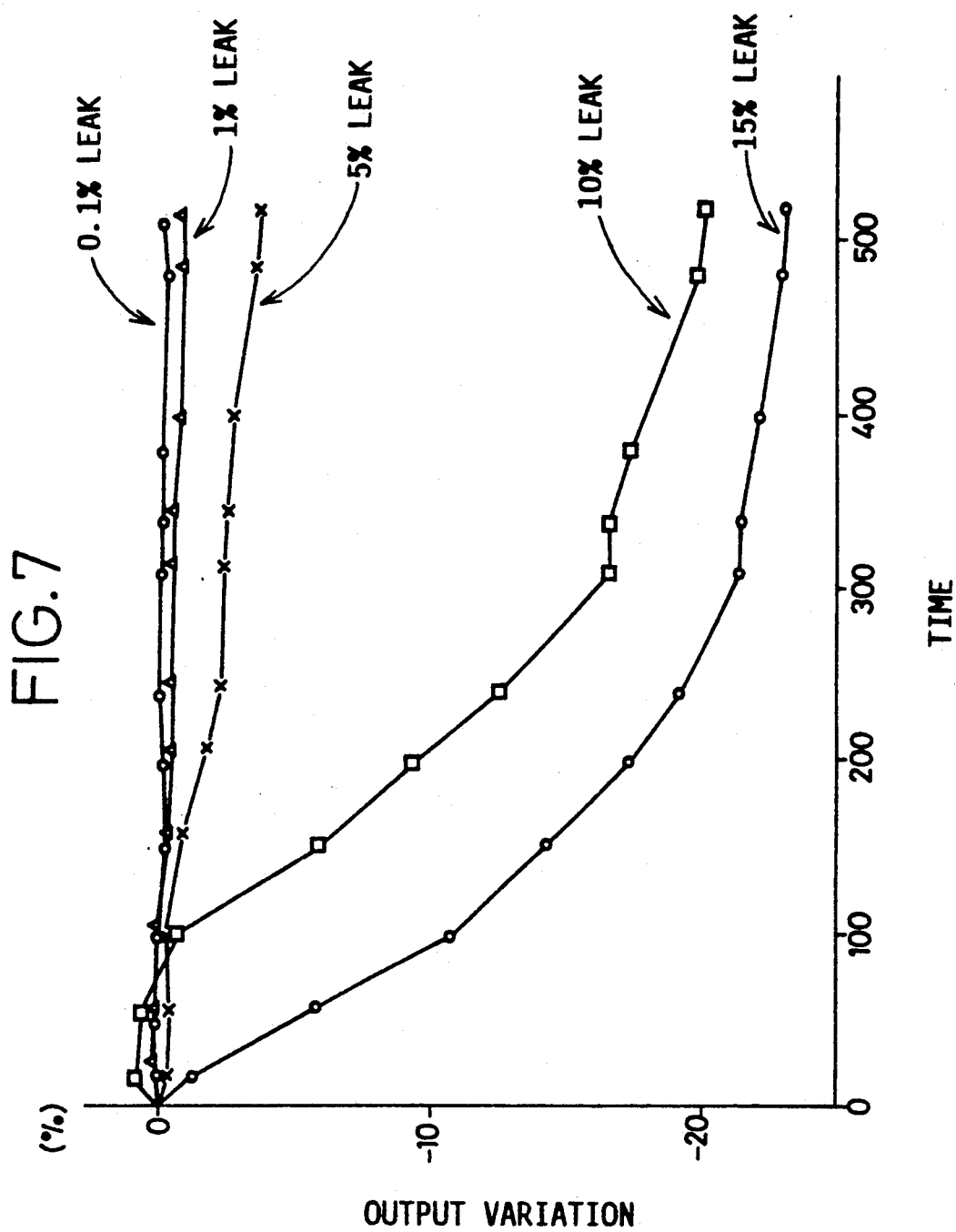

To test the output characteristics and sensing accuracy of the oxygen sensor constructed as described above, there were prepared some specimens of the sensors having different ratios (Ip'/Ip) of the leak current to the overall pump current, which ratios range from 0% to 15%. The results of the tests are indicated in the graphs of FIGS. 4 through 7. In the test of FIG. 4, the amount of the leak pump current was controlled so that a first group of specimens had a ratio (Ip'/Ip) of not higher than 5%, and a second group of specimens had a ratio (Ip'/Ip) of not higher than 15%. FIG. 4 shows a variation in the output values of each group of the specimens in relation to varying oxygen concentration of the measurement gas. In FIG. 4, the variation in the output values of the first group is indicated by a solid line, while that of the second group is indicated by a broken line. It is to be understood in the graph of FIG. 4 that the output of the oxygen sensor is 100% when it is exposed to the ambient air. In the test of FIG. 5, the amount of the leak pump current which leaks from the pumping cell 12 was controlled so that the ratios (Ip'/Ip) of the specimens were equal to 0%, 5%, 10% and 15%, respectively. These specimens were tested several times to detect the oxygen concentration of the measurement gas having 10% of oxygen, and the fluctuation in the output produced by each specimen was observed. The result of this test is indicated in the bar graph of FIG. 5. In the test of FIG. 6, the amount of the leak pump current was controlled such that the ratios (Ip'/Ip) of the specimens were equal to 1%, 5%, 10% and 15%, respectively. The bar graph of FIG. 6 shows the rate of variation in the outputs of each specimen when the temperature of the atmosphere to which the specimens were exposed was raised from the room temperature to 500° C. In the test of FIG. 7, the amount of the leak pump current was controlled so that the ratios (Ip'/Ip) of the specimens were equal to 0.1%, 1%, 5%, 10% and 15%, respectively. These specimens were continuously tested to determine the A/F ratio of an air-fuel mixture by sensing the exhaust gases emitted from a diesel engine as a result of combustion of the air-fuel mixture, during the idling operation of the diesel engine. The line graph of FIG. 7 shows the rate of chronological change of the output produced by each specimen.

It will be readily understood from the results of the above-described tests that it is especially advantageous to control the amount of the leak pump current so that the ratio (Ip'/Ip) of the leak current is held within 0.1% ~5% of the overall pump current.

Referring next to the schematic view of FIG. 8, there will be described another embodiment of the oxygen sensor constructed according to the present invention. In the following description, the same numerals as used in the preceding embodiment will be used for identifying structurally and functionally corresponding elements, and no redundant explanation of these elements will be provided.

In the sensing element 10 of the instant oxygen sensor, the measuring electrode 28 of the oxygen sensing cell 14 is connected to neither of the electrodes 18, 20 of the oxygen pumping cell 12, but is directly connected to the external electric circuit through an external connecting terminal. In this external electric circuit for controlling the electrical operation of the sensing element 10, the measuring electrode 28 is grounded, i.e., connected to the reference conductor, via the resistor 56, at a point in a conductor path between the amplifier 76 and the external connecting terminal connected to the measuring electrode 28. As in the preceding embodiment, the potential of the reference conductor to which the measuring electrode 28 is connected via the resistor 56 is equal to the reference potential which is applied to the inner electrode 20 of the oxygen pumping cell 12 so as to permit the pump current to flow between the outer and inner pumping electrodes 18, 20. Namely, the inner pumping electrode 20 is directly grounded to the earth, i.e., reference conductor.

With the external electric circuit constructed as described above, the resistor 56 is provided outside or separately from the sensing element 10 of the sensor. In the oxygen sensor of the instant modified embodiment, too, the amount of the current which leaks from the pump cell 12 toward the measuring electrode 28 can be suitably limited or determined by suitably determining the resistance value of the resistor 56. Thus, the same effects as provided by the oxygen sensor of the first embodiment can be obtained by the oxygen sensor of the present embodiment.

While the present invention has been described in its presently preferred embodiments with a certain degree of particularity, it is to be understood that the invention is not limited to the precise details of the illustrated embodiments.

For example, the oxygen pumping cell 12, the oxygen sensing cell 14 and diffusion resistance means of the sensing element 10 may have various structures or forms, other than those adopted in the illustrated embodiments. More specifically, the gas-inlet aperture 38 may take the form of an orifice passage so that the aperture 38 functions not only as means for introducing the measurement gas into the thin flat space 36, but also as diffusion resistance means having a predetermined resistance to diffusion of the measurement gas.

While the inner pumping electrode 20 of the oxygen pumping cell 12 is grounded so that the electrode 20 has the reference potential, the outer pumping electrode 18 may be grounded so that the outer pumping electrode 18 has the reference potential.

Further, the resistor 56 provided between the measuring electrode 28 and the reference conductor may be formed of any known material. When the resistor 56 is formed integrally with the sensing element 10 as in the first embodiment, the resistor 56 may be a thick-film resistor obtained by firing a thick-film paste which is applied to a sintered body or a green sheet of the sensing element 10 by printing or coating. The thick-film paste may be prepared by admixing a powder of ruthenium oxide and a powder of glass with an organic binder, or by admixing a heat-resistive metal powder such as platinum or platinum-rhodium, and a ceramic powder such as alumina or zirconia, with an organic binder. When the resistor 56 is provided in the external electric circuit as in the second embodiment, the resistor 56 may be a carbon-film resistor or metallic film resistor which is widely used in an ordinary electric circuit.

While the resistor 56 provided in the electric circuit in the second embodiment of FIG. 8 is a fixed resistor, it may be replaced by a variable resistor whose resistance value is adjustable during use of the apparatus, or a semifixed resistor.

When the resistor 56 is formed integrally with the sensing element 10, the resistor 56 may be formed as a film which is embedded in an integral laminar structure of the sensing element 10.

The resistor 56 as described above may be otherwise constructed as long as the resistor functions to provide a suitable potential difference between the measuring electrode 28 and the outer or inner pumping electrode 18, 20 between which the leak current flows, which potential difference is smaller by a given value than the potential difference between the outer and inner pumping electrodes 18, 20 to which the pump current is applied. That is, the resistor need not be apparently recognized as an element disposed on the conductor path between the measuring electrode 28 and the reference conductor having the reference potential. For example, the oxygen sensor according to the second embodiment may have an inverting amplifier 96 including resistors 92, 94, as shown in FIG. 9, instead of the electrical arrangement indicated by an arrow "a" in FIG. 8. Alternatively, the resistor 56 may be replaced by input resistance of an amplifier or a resistance component of a coil or a condenser.

It will be understood that the present invention may be embodied with various changes, modifications and improvements, which may occur to those skilled in the art, without departing from the spirit and scope of the invention defined by the appended claims.

What is claimed is:

1. An air/fuel ratio sensing apparatus for determining an air/fuel ratio of an air-fuel mixture, having a sensing element including an electrochemical oxygen pumping cell having a first oxygen ion-conductive solid electrolyte body and a first and a second electrode which are formed on the first solid electrolyte body, an electrochemical oxygen sensing cell having a second oxygen ion-conductive solid electrolyte body and a third and a fourth electrode which are formed on the second solid electrolyte body, and diffusion-resistance means for introducing exhaust gases produced as a result of combustion of the air-fuel mixture, under a predetermined diffusion resistance, for contact with the second electrode of the pumping cell and the third electrode of the sensing cell, said apparatus comprising:
   means for connecting one of said first and second electrodes of said oxygen pumping cell to a reference conductor having a reference potential for permitting a pump current to flow through said oxygen pumping cell; and
   an electrical resistor provided in a conductor path connecting said third electrode of said sensing cell to said reference conductor, so that an amount of a leak current which leaks from said oxygen pumping cell to said oxygen sensing cell is determined by an electrical resistance value of said electrical resistor.

2. An air/fuel ratio sensing apparatus according to claim 1, wherein said electrical resistor is provided on said sensing element.

3. An air/fuel ratio sensing apparatus according to claim 1, further comprising an electrical circuit which is disposed outside of and electrically connected to said sensing element, said electrical resistor being provided in said electrical circuit.

4. An air/fuel ratio sensing apparatus according to claim 1, wherein said electrical resistance value of said electrical resistor is determined such that a ratio of the amount of said leak current to an overall amount of said pump current applied to said oxygen pumping cell is within a range of 0.1–5%.

5. An air/fuel ratio sensing apparatus according to claim 4, wherein said electrical resistance value is determined such that said ratio is within a range of 0.5–3%.

6. An air/fuel ratio sensing apparatus according to claim 1, wherein said second electrode of said oxygen pumping cell is connected to said reference conductor.

7. An air/fuel ratio sensing apparatus according to claim 1, wherein said third electrode of said oxygen sensing cell is connected via said electrical resistor to the earth as said reference conductor.

8. An air/fuel ratio sensing apparatus according to claim 1, wherein said one of said first and second electrodes of said oxygen pumping cell is connected to said third electrode of said oxygen sensing cell via said electrical resistor.

9. An air/fuel ratio sensing apparatus according to claim 1, further comprising a heater having a heat-generating element for heating said oxygen pumping and sensing cells, and a heater power source connected to said heat-generating element through a terminal for energizing said heat-generating element, said electrical resistor being connected to said reference conductor via said terminal.

10. An air/fuel ratio sensing apparatus according to claim 1, further comprising a differential amplifier which is connected to said third and fourth electrodes of said oxygen sensing cell and which produces an output indicative of an electromotive force induced between said third and fourth electrodes, said electrical resistor being connected to a conductor path between said third electrode and said differential amplifier.

11. An air/fuel ratio sensing apparatus according to claim 1, further comprising a connecting solid electrolyte body interposed between said first and second solid electrolyte bodies of said oxygen pumping and sensing cells, said connecting solid electrolyte body and said first and second solid electrolyte bodies cooperate to define a gas-diffusion space as said diffusion resistance means.

12. An air/fuel ratio sensing apparatus according to claim 11, wherein said gas-diffusion space is a thin flat space, and said second and third electrodes of said oxygen pumping and sensing cells are disposed opposite to each other in a direction of thickness of said thin flat space, so as to partially define said thin flat space.

13. An air/fuel ratio sensing apparatus for determining an air/fuel ratio of an air-fuel mixture, having a sensing element including an electrochemical oxygen pumping cell having a first oxygen ion-conductive solid electrolyte body and a first and a second electrode which are formed on the first solid electrolyte body, an electrochemical oxygen sensing cell having a second oxygen ion-conductive solid electrolyte body and at third and a fourth electrode which are formed on the second solid electrolyte body, and diffusion-resistance means for introducing exhaust gases produced as a result of combustion of the air-fuel mixture, under a predetermined diffusion resistance, for contact with the second electrode of the pumping cell and the third electrode of the sensing cell, said apparatus comprising:

means for connecting one of said first and second electrodes of said oxygen pumping cell to a reference conductor having a reference potential for permitting a pump current to flow through said oxygen pumping cell; and means for controlling an amount of leak current which leaks from said oxygen pumping cell to said oxygen sensing cell, said means being provided in a conductor path connecting said third electrode of said sensing cell to said reference conductor.

14. An air/fuel ratio sensing apparatus according to claim 13, wherin said means for controlling an amount of leak current comprises an electrical resistor, the electrical resistance value of which is selected to limit said leak current to a certain value.

* * * * *